United States Patent [19]

Harrigan et al.

[11] Patent Number: 4,795,176

[45] Date of Patent: Jan. 3, 1989

[54] MODESTY RESTRAINT FOR TOILET CHAIRS

[76] Inventors: Linda M. Harrigan, 1201 Eric Ct., Rohnert Park, Calif. 94928; Marlene H. Jaworski, 906 Smith, Alturas, Calif. 96101

[21] Appl. No.: 150,838

[22] Filed: Feb. 1, 1988

[51] Int. Cl.⁴ .............................................. A47C 31/00
[52] U.S. Cl. ................................... 297/465; 128/873; 297/485; 297/DIG. 4
[58] Field of Search ................ 297/465, 466, DIG. 4, 297/485; 128/134, 133; 4/483

[56] References Cited

U.S. PATENT DOCUMENTS

| 1,837,983 | 12/1931 | Moran | 297/465 X |
| 4,341,421 | 7/1982 | Rowley | 297/465 |
| 4,510,631 | 4/1985 | Grady | 297/DIG. 4 |

FOREIGN PATENT DOCUMENTS 2279588  2/1976  France .................. 297/466

Primary Examiner—James T. McCall

[57] ABSTRACT

A fabric support and restraint garment designed to safely and comfortably retain a person to a portable commode chair while providing proper body alignment. The device is constructed of a front torso panel with V-neck opening in the top and has a shoulder flap extension of the panel to the back. The torso panel is attached on the lower edge to a pelvic panel which covers only the front of the pelvic area. The pelvic panel contains two leg openings, located on the lower edge, which are created by the partial attachment of two rib knit leg bands. These bands are attached to the pelvic panel only on the top half, leaving the other half free to pass behind the thigh. Inadvertent removal of the garment by the wearer is prevented by four straps attached to the lower sides of the garment which are wound around the frame of the chair and tied behind the person on the shoulder flap extension.

4 Claims, 2 Drawing Sheets

MODESTY RESTRAINT FOR TOILET CHAIRS

BACKGROUND OF THE INVENTION

1. Field of the Invention

This invention relates to support and restraint devices designed to be used on mentally and or physically incapacitated people to prevent falls and subsequent injury while using portable commode chairs.

2. Description of the Prior Art

Past art patents were examined from a search conducted in the following classes and subclasses: 4/457, 297/465 and 483.

Patents which were found to be most pertinent to my invention included: U.S. Pat. No. 2,170,703, dated Aug. 22, 1939, issued to Waxman et al, discloses a child bid and restraint Nigro was issued U.S. Pat. No. 2,635,245, dated Apr. 21, 1953, and illustrates a combination garment and safety On Oct. 23, 1956, Givens was issued U.S. Pat. No. 2,767,403 for child tie-in-bibs.

The Jordan patent was issued on Sept. 27, 1977, U.S. Pat. No. 4,050,737, for a chair support harness for children.

U.S. Pat. No. 4,235,474 was issued on Nov. 25, 1980 to Rosenberg for a chair restraint for infants.

Rowley was issued U.S. Pat. No. 4,341,421, on July 27, 1982, for a child restraining article.

On Jan. 31, 1984, Elf was issued U.S. Pat. No. 4,428,514, for a wearable infant carrier.

To my knowledge, the foregoing patents represented devices most pertinent to my invention. Although my device is a support and restraint garment, as are most of the past art patents, my device is specifically designed for safely restraining a person on a portable commode chair. None of the previous inventions disclosed restraints to be used for a person on a commode chair. No devices seen could even be effectively used in that manner. Most restraint and support devices currently available are designed to be used to retain a person in a chair, a wheelchair, or in a bed. Complications arise when these restraints are used to confine a person to a portable commode. The results is generally an ineffective and unsafe procedure. My device overcomes these problems safely and easily, and I therefore feel it is a definite improvement over those patent disclosures previously mentioned.

SUMMARY OF THE INVENTION

In practicing my invention, I have developed a support and restraint garment which is specifically designed to retain an incapacitated person to a portable commode chair. My device is structured in a two piece garment with attached straps and arranged for concealing the pelvic area, front body portion and shoulders of a human patient when in use. The material used is a washable and dryable durable fabric. The garment has a front panel which has a neck opening to the top, and a shoulder flap extension to the back. The front panel is sewn with a gathered seam to a pelvic panel which covers only the front portion of the person's torso, but which has attached leg bands to secure the garment in place. Four attached straps and two strap guides hold the garment in place and when the straps are secured around the frame of a portable toilet chair and tied to the shoulder flap, they safely retain the wearer in a seated position. The shoulder flap and straps are passed over the back of the portable toilet chair backrest and when secured, prevent the wearer from falling forward, slipping down, or falling sideways.

Therefore, it is a primary object of my invention to provide a device which can be effectively used to safely restrain a person while using a portable commode chair, thereby preventing falls and possible injury.

Another object of my invention is to provide a device which helps to support a person seated on a portable commode chair in proper body alignment by preventing the person from sliding down off the commode, leaning to one side, or falling forward.

A further object of my invention is to provide a restraint and support device for portable commode chairs which modestly shields the wearer by covering the front torso area of the body.

A still further object of my invention is to provide a restraint garment which is comfortable and avoids constriction of any part of the body, thereby avoiding pressure sores or tissue damage.

A even further object of my invention is to provide a support and restraint garment which is durable and machine washable and dryable.

These object and other advantages of my device will appear evident with a reading of the following description and comparison of the number parts with those of the accompanying drawings.

Figure 1:
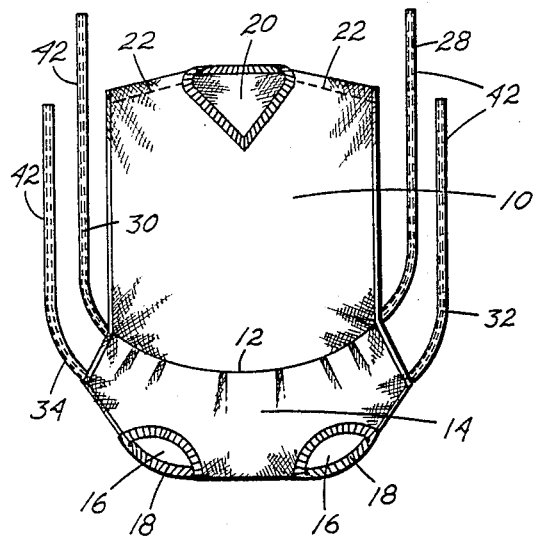
FIG. 1 a frontal view of the preferred embodiment of the invention.

DRAWING REFERENCE NUMBERS 10 front panel
12 gathered seam
14 pelvic panel
16 leg openings
18 elastic rib knit band
20 V-neck opening
22 shoulder darts
24 shoulder flap
26 strap guides
28 left upper strap
30 right upper strap
32 left lower strap
34 right lower strap
36 person
38 commode chair
40 vertical frame
42 reinforced strap

DESCRIPTION OF THE PREFERRED EMBODIMENT

Figure 2:
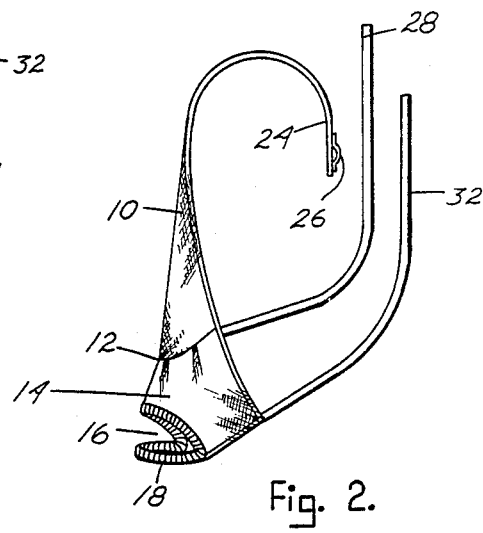
FIG. 2 shows a side view of the device.
Figure 3:
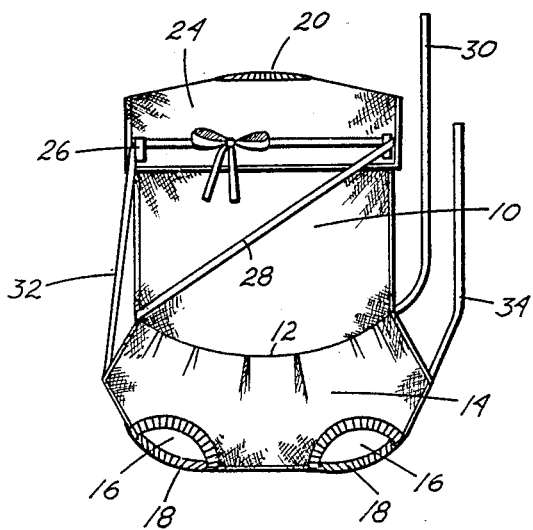
FIG. 3 illustrates rates a rear view of the invention showing the in use strap tieing arrangement on the left.
Figure 4:
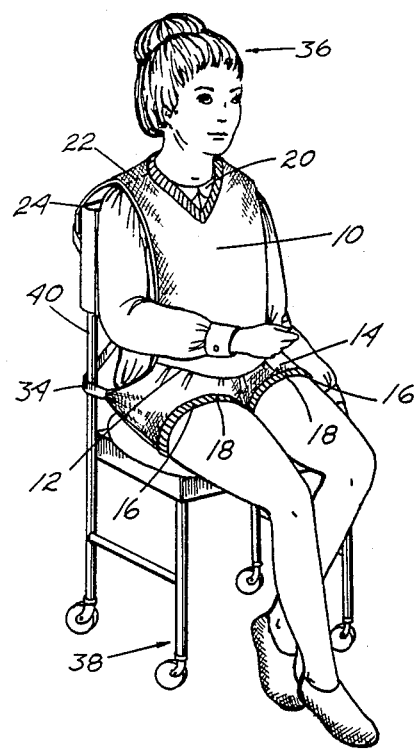
FIG. 4 illustrates a front perspective view of the invention in use, safely retaining a person to a portable commode chair.
Figure 5:
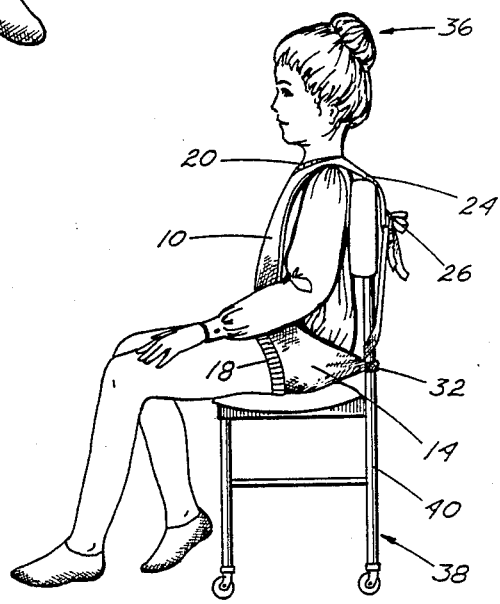
FIG. 5 shows a left side view of the invention in use, showing the bottom tie being wound around the vertical commode chair frame and then tieing to the top shoulder strap.

Referring now to the drawing at FIG. 1 where the preferred embodiment of the invention is shown in an assembled front view. The preferred embodiment is constructed of a two piece, durable, pliable material, the main body of which consists of a rectangular, vertically positioned front panel 10. Front panel 10 is permanently attached, on its lower edge, by gathered seam 12 to the top edge of pelvic panel 14. Two leg openings 16, constructed of elastic rib-knit bands 18, are centrally located on the lower edge of pelvic panel 14. The top half of elastic rib-knit bands 18 are permanently attached to the lower boarder of pelvic panel 14, but the lower half remains detached. Front panel 10 contains V-neck opening 20 which is centrally located on the upper portion of the garment between shoulder darts 22. Shoulder flap 24, a posterior extension of front panel 10, contains on its outward edge, two vertically positioned fabric strap guides 26, as seen in FIG. 2 and 3. Four elongated straps are permanently attached to the lower edge portion of the assembled embodiment, and include left upper strap 28, and right upper strap 30, both of which are attached to each end of gathered seam 12 of the lower portion of front panel 10. Left lower strap 32 and right lower strap 34 are permanently attached to the upper corner portions of pelvic panel 14, as seen in FIGS. 1, 2, and 3.

When applying the assembled embodiment to person 36, the legs are passed through leg openings 16 and the garment is pulled up to the torso where the head is passed through V-neck opening 20 and shoulder flap 24 is positioned behind person 36, over the shoulders. The person sits on commode chair 38 where left lower strap 32 is wrapped around vertical frame 40 of the commode chair 38 and is brought up and through the left strap guide 26. Left upper strap 28 is crossed over the back of person 36, through the right strap guide 26 and is tied to the end of left upper strap 28. The same procedure is followed, from right to left, on the other side of the garment.

Reinforced strap 42 is a second strap embodiment, and consists of heavy but pliable material reinforced with nylon cord.

Although I have described my invention in detail the foregoing is to be considered illustrative only of the principals of the invention, therefore modifications and improvements may be made in the device which do not exceed the intended scope of the appended claims.

I claim:

1. A support and restraint device for the purpose of retaining a human patient in a seated position while using portable commode chairs, comprising:

a two piece durable cloth garment structured to encompass multiple sizes and variations in body shapes and arranged for concealing the pelvic area, front body portion and shoulders of a human patient;

said garment having a first section, being a substantially rectangular fabric front panel, which is attached to a second section, being a smaller rectangular pelvic panel, with said garment having means for attachment to said human patient and for attachment to said commode chair;

said attachment means comprising four elongated straps permanently attached to the edges of said panels, two of the said straps being attached to the lower portion of said front panel and two of said straps being attached to the upper portion of said pelvic panel, said front panel having a fold over shoulder flap extension, a rib-knit V-neck opening in the top, and two darts on either side of said V-neck opening with said front panel attached to said pelvic panel by a gathered seam;

said pelvic panel having two horizontal aligned, downwardly positioned half circular openings attached to circular ribbon of rib-knit fabric to produce round leg openings.

2. The device of claim 1 wherein said shoulder flap fold over extension has two rectangular strap loops affixed to the lower outward edge thereof.

3. The device of claim 1 wherein said four fabric straps are structured of cord reinforced fabric.

4. The device of claim 1 wherein said garment is structured of a durable, machine washable and dryable fabric or lightweight canvas.

* * * * *